US009192694B2

(12) United States Patent
Kyomoto et al.

(10) Patent No.: US 9,192,694 B2
(45) Date of Patent: Nov. 24, 2015

(54) BIOCOMPATIBLE AND LOW-ABRASION MEMBER, AND ARTIFICIAL JOINT USING THE SAME AND METHOD OF PRODUCING THE SAME

(75) Inventors: Masayuki Kyomoto, Osaka (JP); Kazuhiko Ishihara, Tokyo (JP); Kozo Nakamura, Tokyo (JP); Yoshio Takatori, Tokyo (JP); Hiroshi Kawaguchi, Tokyo (JP); Toru Moro, Tokyo (JP)

(73) Assignees: KYOCERA MEDICAL CORPORATION, Osaka (JP); THE UNIVERSITY OF TOKYO, Tokyo (JP)

( * ) Notice: Subject to any disclaimer, the term of this patent is extended or adjusted under 35 U.S.C. 154(b) by 1260 days.

(21) Appl. No.: 12/733,976

(22) PCT Filed: Oct. 2, 2008

(86) PCT No.: PCT/JP2008/067941
§ 371 (c)(1),
(2), (4) Date: Sep. 29, 2011

(87) PCT Pub. No.: WO2009/044816
PCT Pub. Date: Apr. 9, 2009

(65) Prior Publication Data
US 2012/0197413 A1    Aug. 2, 2012

(30) Foreign Application Priority Data

Oct. 3, 2007  (JP) .................... 2007-260191
Jan. 23, 2008  (JP) .................... 2008-012794

(51) Int. Cl.
*A61F 2/30*   (2006.01)
*A61L 27/34*  (2006.01)
(Continued)

(52) U.S. Cl.
CPC ............. *A61L 27/34* (2013.01); *A61L 27/50* (2013.01); *A61F 2/32* (2013.01); *A61F 2/38* (2013.01);
(Continued)

(58) Field of Classification Search
None
See application file for complete search history.

(56) References Cited

U.S. PATENT DOCUMENTS

2002/0017455 A1   2/2002  Kirkpatrick et al.
2004/0243249 A1   12/2004 Ishihara et al.
(Continued)

FOREIGN PATENT DOCUMENTS

JP   2003-310649   11/2003
JP   2004-502514   1/2004
(Continued)

OTHER PUBLICATIONS

International Search Report issued Dec. 9, 2008 in International (PCT) Application No. PCT/JP2008/067941.
(Continued)

*Primary Examiner* — Thomas J Sweet
*Assistant Examiner* — Rebecca Preston
(74) *Attorney, Agent, or Firm* — Wenderoth, Lind & Ponack, L.L.P.

(57) ABSTRACT

The object of the present invention is to provide a sliding member, a prosthesis and a method of producing the sliding member, which can suppress production of abrasive wear debris by suppressing friction of the sliding section, and also can maintain satisfactory mechanical characteristics in vivo. A sliding member comprising: a substrate 1 capable of forming hydroxyl groups; and a biocompatible material layer 4 laminated on appropriate sections of the substrate 1, wherein hydroxyl groups are formed on at least a required section of a surface of the substrate 1 by surface treating to form a surface-treated layer 2, while the biocompatible material layer 4 is formed from a polymer containing phosphorylcholine groups, and wherein the substrate 1 and the biocompatible material layer 4 are joined via a binder layer 3 formed from silica being covalently bonded with the hydroxyl groups and the biocompatible material, respectively.

23 Claims, 6 Drawing Sheets

(51) Int. Cl.
*A61L 27/50* (2006.01)
*A61F 2/32* (2006.01)
*A61F 2/38* (2006.01)
*A61F 2/40* (2006.01)
*A61F 2/42* (2006.01)
*A61F 2/44* (2006.01)

(52) U.S. Cl.
CPC .... *A61F 2/40* (2013.01); *A61F 2/42* (2013.01); *A61F 2/44* (2013.01); *A61F 2002/30003* (2013.01); *A61F 2002/30026* (2013.01); *A61F 2002/30065* (2013.01); *A61F 2002/30673* (2013.01); *A61F 2002/30685* (2013.01); *A61F 2002/30934* (2013.01); *A61F 2002/30971* (2013.01); *A61F 2310/00011* (2013.01); *A61F 2310/00023* (2013.01); *A61F 2310/00029* (2013.01); *A61F 2310/00179* (2013.01); *A61F 2310/00389* (2013.01); *A61F 2310/00916* (2013.01); *A61F 2310/00976* (2013.01); *A61L 2400/18* (2013.01); *A61L 2430/24* (2013.01)

(56) References Cited

U.S. PATENT DOCUMENTS

| | | | |
|---|---|---|---|
| 2005/0241736 | A1 | 11/2005 | Bell et al. |
| 2006/0060533 | A1* | 3/2006 | Miyazawa et al. ............ 210/656 |
| 2006/0286140 | A1 | 12/2006 | Wickstrom et al. |
| 2007/0054127 | A1* | 3/2007 | Hergenrother et al. .... 428/411.1 |
| 2007/0207321 | A1 | 9/2007 | Abe et al. |
| 2007/0299511 | A1* | 12/2007 | Gale ........................... 623/1.46 |
| 2008/0292778 | A1* | 11/2008 | Tarcha et al. ................. 427/2.25 |
| 2009/0317443 | A1* | 12/2009 | Willis et al. .................. 424/423 |

FOREIGN PATENT DOCUMENTS

| | | |
|---|---|---|
| JP | 2005-524772 | 8/2005 |
| JP | 2006-000219 | 1/2006 |
| JP | 2006-089778 | 4/2006 |
| JP | 2007-031408 | 2/2007 |
| JP | 2007-505697 | 3/2007 |
| JP | 2007-195883 | 8/2007 |
| JP | 2007-202965 | 8/2007 |
| WO | 02/04696 | 1/2002 |
| WO | 2005/097673 | 10/2005 |
| WO | 2007/091521 | 8/2007 |

OTHER PUBLICATIONS

International Preliminary Report on Patentability and Written Opinion issued May 4, 2010 in International (PCT) Application No. PCT/JP2008/067941 of which the present application is the national stage.

European Search Report issued Dec. 4, 2012 in corresponding European Patent Application No. 08 83 6671.

Y. Wang et al., "Covalent coupling of an phospholipid monolayer on the surface of ceramic materials", Chem. Commun., 2000, pp. 587-588.

Office Action issued Jun. 4, 2013 in corresponding Japanese Application No. 2009-536083.

Wei Feng et al., "Adsorption of Fibrinogen and Lysozyme on Silicon Grafted with Poly-(2-methacryloyloxyethyl Phosphorylcholine) via Surface-Initiated Transfer Radical Polymerization", Langmuir, vol. 21, 2005, pp. 5980-5987.

Emma M. E. Kristensen et al., "Photoelectron Spectroscopy Studies of the Functionalization of a Silicon Surface with a Phosphorylcholine-Terminated Polymer Grafted onto (3-Aminopropyl)trimethoxysilane", Langmuir, vol. 22, 2006, pp. 9651-9657.

Gongneng Cailiao, vol. 38, No. 4, 2007, pp. 623-625.

Hiroki Ohno et al., "ESCA Study on Improvements in Adhesive Ability of Dental Adhesive Resin to Ni—Cr Alloy Treated by $HNO_3$ Solution", Higashi Nippon Dental Journal, vol. 6, No. 2, Dec. 1987, pp. 103-111.

Masayuki Kyomoto et al., "High lubricious surface of cobalt-chromium-molybdenum alloy prepared by grafting poly(2-methacryloyloxyethyl phosphorylcholine)", Biomaterials, vol. 28, Mar. 18, 2007, pp. 3121-3130.

\* cited by examiner

Untreated Co-Cr-Mo

Co-Cr-Mo-g-MPC
0.25 mol/L, 90 minutes

Poly (MPC) layer, 10 nm

Co-Cr-Mo-g-MPC
0.50 mol/L, 90 minutes

Poly (MPC) layer, 100 nm

BIOCOMPATIBLE AND LOW-ABRASION MEMBER, AND ARTIFICIAL JOINT USING THE SAME AND METHOD OF PRODUCING THE SAME

TECHNICAL FIELD

The present invention relates to a sliding member which can impart a lubricated state to the sliding section, and a biomaterial using the same, which exhibits hydrophilicity and biocompatibility. In particular, the present invention relates to an artificial joint acting as a prosthesis for a human joint.

BACKGROUND ART

The sliding member aims at sliding on the sliding surface of the femoral head or the cup of an artificial joint, and is particularly suited for use in vivo.

High-strength materials such as metals or ceramics are widely used in medical fields as prosthesis covering fractured sections, such as bone prosthesis or dental prosthesis (artificial dental roots) or as prosthesis for a physical activity, such as joint prostheses. Recent developments have seen the active application of metals to artificial circulatory system. Consequently, there is a need for materials with mechanical strength as well as biocompatibility. Here the term "biocompatibility" means the property of preventing blood coagulation reactions or suitable adaptability of the inserted section to soft tissue. This sort of biocompatibility is indispensable for in vivo medical devices.

A technique is known of applying 2-methacryloyloxyethyl phosphorylcholine (hereinafter referred to as "MPC") which has superior biocompatibility as a medical polymer material. Conventionally, many biocompatible MPC polymers have been used in the form of an MPC copolymer containing hydrophobic groups resulting from the copolymerization of MPC with monomers containing hydrophobic groups. However in case that the resulting copolymer is coated onto the surface of the substrate ("surface substrate") to be used in a medical device, few problems have, if in a short timeframe, arisen by being contacted with blood. However it is quite likely for the coating to remove from the surface substrate during long-term use.

In order to avoid these problems, a technique has been disclosed in which a coating material containing a copolymer of a reactive co-monomer, such as a stryrene monomer containing amino groups or methylacrylate containing amino groups, as well as a monomer containing phosphorylcholine analogous groups has been used to fix this copolymer covalently to the substrate surface (Patent Document 1). However this technique has not generally been commercially applied due to the high price of stryrene monomers containing amino groups or methylacrylate containing amino groups.

Another method has been disclosed in which chemical bonding is used to fix an MPC copolymer containing amino groups as well as an MPC copolymer containing epoxy groups to the surface substrate in a medical device (Patent Document 2 and Patent Document 3). However difficulties have been encountered in fixing the MPC copolymer containing amino groups to the substrate surface depending on the ratio of amino group content. As a result, the coating may become fragile.

A method has been disclosed in which a random copolymer comprising allylamine and phosphorylcholine analogue groups is fixed to a medical device (Patent Document 4). For example, in case that a coated medical device is made of a metallic material, a polymer 4-methacryloxyethyltrimellitate anhydride (hereinafter referred to as "4-META") is used as a binder. The acid anhydride group contained in the 4-META polymer has superior reactivity with respect to an amino group in the random copolymer formed from allylamine and phosphorylcholine analogous groups. Consequently this binder enables a random copolymer to be fixed to the medical biomaterial.

However, as described above, when the copolymer is used, the content of phosphorylcholine groups decreases and there arises a problem that biocompatibility, hydrophilicity and surface lubricity deteriorate. In contrast, when the content of phosphorylcholine groups is too large, the copolymer becomes water soluble and there arises a problem that the copolymer is not fixed when used for a long time. Actually, an artificial heart formed from titanium metal coated with an MPC copolymer contains no more than 30% of MPC therein because of the problem of solubility (Non-Patent Document 1).

Joint prostheses such as knee joint prostheses or hip joint prostheses have been used which are generally constructed by a combination of ultra-high molecular weight polyethylene (hereinafter referred to as "UHMWPE") and a cobalt-chromium (hereinafter referred to as "Co—Cr") alloy. However in case that joint prostheses are used in vivo, UHMWPE wear debris produced by frictional motion entered between the acetabular cup and the living bone. The wear debris are engulfed by macrophages, osteolytic cytokines are released leading to possibility of inducing osteolysis. Osteolysis leads to the serious problem that the fixing strength between the joint prosthesis and the bone is weakened, thus resulting in a complication concerning joint arthroplasty, which is termed as loosening (Non-Patent Document 2).

Normally the linear wear of the UHMWPE ranges from 0.1 mm to 0.2 mm annually and therefore no problems arise immediately after joint arthroplasty. However after approximately five years, aseptic loosening occurs as described above. It is sometimes the case that the joint prostheses should be replaced, leading to a large burden on the patient.

A method of solving the problem of loosening is to reduce the amount of UHMWPE wear debris. Therefore various tests have been performed for the purpose of improving the combination of the material used on the joint surface or improving the material itself. Especially, UHMWPE cross-linked by means of an electron beam or a radioactive-ray (cross-linked polyethylene, hereinafter referred to as "CLPE") has been actively researched in recent years.

Research is also being conducted to improve the bearing surface of UHMWPE or the like. The group led by Nobuyuki Yamamoto has produced a medical device having the biocompatibility and the surface lubricity, which is produced by fixing a random copolymer comprising allylamine and phosphorylcholine analogue groups to the surface of a medical device including a joint prosthesis (Patent Document 4). The group led by Kazuhiko Ishihara has produced a joint prosthesis in which polymer material is used which grafts polymerizable monomers containing a phosphorylcholine group onto a polymer joint prosthesis containing UHMWPE, thus suppressing the production of wear debris by reducing friction between the bearing surface of the joint prosthesis (Patent Document 5).

It has also been proposed to use a combination of hard-material members at the joint interface instead of using polymer materials such as UHMWPE which can create abrasion. For example, a joint prosthesis is currently undergoing clinical uses, which is formed from a combination of a femoral head prosthesis made of a Co—Cr alloy and an acetabular cup prosthesis made of Co—Cr alloy (Non-Patent Document 3) or a combination of a femoral head prosthesis made of an alumina-ceramic and an acetabular cup prosthesis made of an alumina-ceramic (Non-Patent Document 4).

Patent Document 1: Japanese Unexamined Patent Publication (Kokai) No. 7-502053

Patent Document 2: Japanese Unexamined Patent Publication (Kokai) No. 7-184989

Patent Document 3: Japanese Unexamined Patent Publication (Kokai) No. 7-184990

Patent Document 4: International Publication No. WO 01/05855, pamphlet

Patent Document 5: Japanese Patent Unexamined Publication (Kokai) No. 2003-310649

Non-Patent Document 1: "In Vivo Evaluation of a MPC Polymer Coated Continuous Flow Left Ventricular Assist System" ARTIFICIAL ORGANS, VOL27, No. 2, 2003

Non-Patent Document 2: "In vivo wear of polyethylene acetabular components" THE JOURNAL OF BONE AND JOINT SURGERY, VOL75-B, No. 2, 1993

Non-Patent Document 3: "Engineering Issues and Wear Performance of Metal on Metal Hip Implants" CLINICAL ORTHOPAEDICS AND RELATED RESEARCH, No. 333, 1996

Non-Patent Document 4: "Wear rates of ceramic-on-ceramic bearing surfaces in total hip implants: A 12-year follow-up study" THE JOURNAL OF ALTHROPLASTY, VOL 14, No. 7, 1999

SUMMARY OF THE INVENTION

However in case that a random copolymer comprising allylamine and phosphorylcholine analogue groups is applied to the surface of a medical device, the random copolymer has been sufficiently pre-polymerized not to be fixed to the surface of the medical device (corresponding to the substrate according to the present invention). Therefore, there is insufficient bonding between the random copolymer and the surface of the medical device. Consequently unsatisfactory results are obtained in case that the above prosthesis is used for a long time in vivo, and in particular, under the rigorous friction and wear environment of the bearing surface of a joint prosthesis. Even though it is likely for UHMWPE to be generally used as a bearing material in polymer joint prosthesis, it does not contain functional groups such as carboxyl groups, carboxylic acid anhydrides, epoxy groups, isocyanate groups to therefore have conspicuously poor binding to random copolymers comprising allylamine and phosphorylcholine analogue groups. In order to solve this problem, it has been suggested to treat the surface of the medical device by means of plasma treatment, corona treatment, ozone treatment or the like to provide carboxyl groups with the surface. However such treatments unavoidably affect the characteristics of the substrate of the medical device and unsatisfactory results are obtained. Although surface lubricity or biocompatibility can be provided by fixing a random copolymer comprising allylamine and phosphorylcholine analogue groups to the surface of the medical device, long-term wear-resistance characteristics which are the most important problem regarding bearing materials for polymer joint prostheses are not solved thereby. Furthermore in case that a coated medical device is made of a metallic material, if a 4-META polymer is used as a binder, the acid anhydride group contained in the 4-META polymer has superior reactivity by means of the random copolymer comprising allylamine and phosphorylcholine analogue groups. These random copolymers bind to the medical biomaterial via the binder. However the acid anhydride group contained in the 4-META polymer binds to the random copolymer at the same time as binding to the substrate. Thus the problem arises that if the bond to the random copolymer is strong, the bond with the substrate will become fragile. On the other hand, if the bond with the substrate is strong, the bond with the random copolymer will be fragile.

As described above, the Ishihara group graft-bonded MPC which is a polymerizable monomer comprising phosphorylcholine groups to UHMWPE which is a polymer material for joint prostheses by irradiating for 30 minutes using ultraviolet (UV) radiation at a wavelength of 300 to 400 nm. The frictional coefficient was considerably reduced as a result of the improvement in wettability. Furthermore superior abrasion characteristics were shown by a study examining sliding over 3 million cycles using a hip joint simulator. However according to hemi-arthroplasty with no acetabular cups replaced, a UHMWPE component is not used and therefore no effect is obtained. In particular, there remain concerns regarding durability in case of knee joint prostheses placed under a high surface contact-pressure condition.

Wear debris produced by friction between Co—Cr alloy components is highly cytotoxic and therefore there are safety concerns in case of use for a long term. Alumina-ceramic material used in combinations of alumina-ceramic femoral head prostheses and alumina-ceramic acetabular cup prostheses as described above is a brittle material to be sometimes broken down during surgical procedures or during in vivo use. Consequently there is a need for further improvement in order to put the same into practical use. These hard materials have poor elasticity and no cushioning function in contrast with for example, UHMWPE. Therefore these materials are not preferred since there is no damping action with respect to external forces and loads are directly applied to the bone.

The present invention is proposed to solve the above problems and has the object of providing a sliding member which can suppress production of abrasive wear debris by suppressing friction of the sliding section, and also can maintain satisfactory mechanical characteristics in vivo.

Means for Solving the Problems

The present inventors performed diligent research into the above problems and made the discovery that although it is difficult to strongly bind a biocompatible material such as MPC to a surface of a substrate, when the substrate surface is properly treated and a binder layer formed from silica is formed on the treated substrate surface and then a layer formed from a biocompatible material is laminated on the binder layer, a biocompatible material layer can be strongly bound to the substrate, thereby making it possible to provide a sliding member having mechanical stability, thus completing the present invention.

In other words, the present invention is a sliding member including a substrate capable of forming hydroxyl groups, and a biocompatible material layer laminated on an appropriate section of the substrate, wherein hydroxyl groups are formed on at least a required position of the surface of the substrate by surface treating, while the biocompatible material layer is formed from a polymer containing phosphorylcholine groups, and wherein the substrate and the biocompatible material layer are joined via a binder layer formed from silica which is covalently bonded with the hydroxyl groups and is also covalently bonded with the biocompatible material.

Also, the present invention is a method of producing sliding member in which a biocompatible material layer is laminated at an appropriate position of a substrate, the method including the steps of:

(a) subjecting a substrate formed from a material containing a metal component capable of forming hydroxyl groups to a surface treatment to form hydroxyl groups on the surface of the substrate;

(b) forming a binder layer formed from silica containing a photo-polymerization initiator on the substrate using the hydroxyl groups as starting points; and (c) immersing the substrate in a solution containing a biocompatible material and polymerizing the biocompatible material at an appropriate position by irradiation with UV radiation to form a biocompatible material layer on the binder layer.

Effects of the Invention

According to the present invention, since a biocompatible material layer is laminated on an appropriate section of a substrate, production of abrasive wear debris can be suppressed by suppressing friction of the sliding section. Since the substrate and the biocompatible material layer are joined via a binder layer formed from silica which is covalently bonded with the hydroxyl groups and is also covalently bonded with the biocompatible material, strong joining of the substrate with the biocompatible material layer can be realized.

Therefore, according to the present invention, it is possible to suppress production of abrasive wear debris by suppressing friction of the sliding section, and to provide a sliding member which can maintain satisfactory mechanical characteristics in vivo, an artificial joint and a method of producing the same.

BEST MODE FOR CARRYING OUT THE INVENTION

The sliding member of embodiments according to the present invention will be described in detail with reference to the accompanying drawings. The embodiments below are merely exemplary and the present invention is not limited to the embodiments.

Embodiment 1

Figure 1:
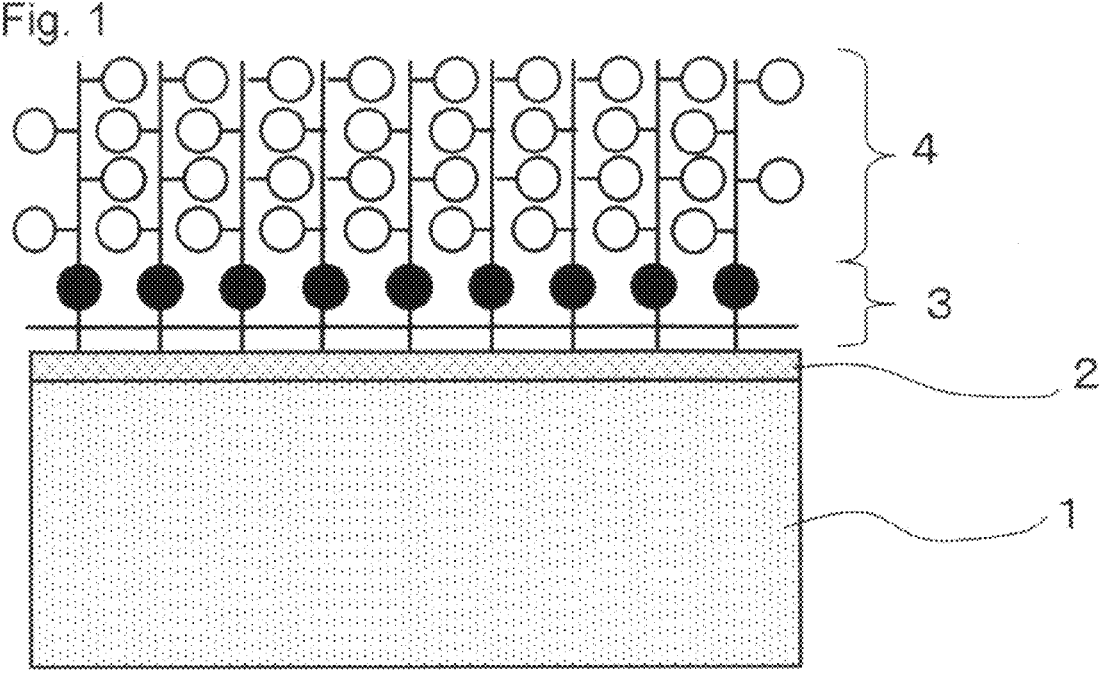
FIG. 1 is a structural view showing the concept of a biomaterial according to the present invention.

FIG. 1 is a schematic sectional view of a sliding member of Embodiment 1 according to the present invention. As shown in FIG. 1, the sliding member according to present Embodiment 1 includes a substrate 1 on which a surface treated layer 2 is formed by treating at least a section of the surface is treated, a binder layer 3 formed from silica laminated on the surface treated layer 2 of the substrate 1, and a biocompatible material layer 4 laminated on the binder layer 3.

The surface treated layer 2 is formed by treating the surface of the substrate 1 with an acid such as nitric acid. By treating the surface of the substrate 1 as described above, hydroxyl groups are formed and the hydroxyl groups serves as starting points of the dehydrating condensation reaction of a silane coupling agent.

First, the silane coupling agent is hydrolyzed to form silanol groups and the silanol groups are bonded with hydroxyl groups contained in the surface treated layer 2 through the dehydrating condensation reaction. Also, other silanol groups contained in the silane coupling agent are bonded with silanol groups of the coupling agent through the dehydrating condensation reaction, and thus this reaction continuously proceeds to form a binder layer 3 formed from silica.

Since methacryloyl groups exist on the surface of the binder layer 3, the methacryloyl groups serve starting points of the growth of a biocompatible material such as MPC. The methacryloyl groups of the biocompatible material on the surface of the binder layer 3 are bonded with functional groups (for example, methacryloyl groups) and, furthermore, the biocompatible material continuously grows to form a biocompatible material layer 4 on the binder layer 3.

As described above, the binder layer 3 formed from silica is strongly bound to the substrate 1 and the biocompatible material layer 4, respectively, via a covalently bonded. Therefore, the substrate 1 and the biocompatible material layer 4 are strongly connected via the binder layer 3, thus making it possible to sufficiently endure an interactive sliding section and to provide an artificial joint having high reliability with high mechanical stability.

Since high-strength materials such as metals, alloys and ceramics are used as the material of the substrate 1, a strong and reliable artificial joint can be achieved.

Furthermore, since the sliding surface of the substrate 1 formed from metals alloys or ceramics is coated with the biocompatible material layer 4, it is possible to suppress production of abrasive wear debris of the substrate 1 that have a fear of an adverse influence of toxicity on the living body. Since the biocompatible material layer 4 is formed from polymeric material such as MPC which does not exert an adverse influence on the living body, no adverse influence is not exert even when abrasive wear debris produces from the biocompatible material layer 4 de to the sliding action.

(Binder Layer)

The binder layer 3 will be described below. As described above, the binder layer 3 enables strong binding of the substrate 1 with the biocompatible material layer 4 and is formed from a silicon alkoxide. Any kind of materials may be used as the silicon alkoxide as long an adverse influence is not exerted on the human body.

The silicon alkoxide used in the binder layer 3 is represented by the general formula: $R^1_x Si(OR^2)_{4-x}$ (X=0 to (3). $OR^2$ at one side is a hydrolysable group and silanol groups (—SiOH) are formed by the hydrolysis reaction. $OR^2$ includes, for example, $CH_3O$—, $C_3H_5O$— and $CH_3OC_2H_4O$—. OH in the silanol groups is hydrophilic polar groups and silanol groups are bonded with each other by the dehydrating condensation reaction. $R^1$ at the other side is an organic functional group and $R^1$ includes, for example, an acryloyl group and a methacryloyl group. The silanol groups (—SiOH) are crosslinked by the dehydrating condensation reaction to form a crosslinking structure called a siloxane network (—Si—O—Si—), and thus a binder layer 3 formed from silica is formed.

Specific examples of the silicon alkoxide used in the binder layer 3 include, methacryloyloxypropyltrimethoxysilane, methacryloyloxypropylmethyldimethoxysilane, methacryloyloxypropyltriethoxysilane and acryloyloxypropyltrimethoxysilane. Taking radical copolymerizability onto consideration, the polymerizable groups is preferably an acryloyl groups or a methacryloyl group.

Biocompatible Material Layer

The biocompatible material layer has the same chemical structure as a cell-membrane constituting biological tissue. As a result, even in the event that wear debris enters the body, the material does not cause a reaction with the internal bodily tissue and thus has no adverse effect on the body. Normally when foreign biological materials such as microorganisms, for example, bacteria or viruses enter a human organism or an organ is transplanted from another person into it, antigen groups on the surface of such foreign material are recognized by antibody molecules or immune cells in the body and provoke a bodily defense reaction, in other words, a rejection reaction. Recognition by the complement system also plays a role in biological reactions to these types of biological foreign materials. The complement system comprises approximately 20 types of blood plasma proteins and is strongly interconnected with other immune system proteins or cells. The complement system has the object of notifying immune system cells of the presence of a foreign material and killing invading microorganisms. The recognition of foreign material results in activation of complement. Consequently the introduction of materials such as bone prosthesis activates complement. When these types of materials are inserted directly into bone, the materials come into contact with biological fluids or the like and protein attaches to the surface of the material. Thus neutrophils and macrophages (phagocytes) are activated and information transmission substances termed cytokines are released. In the interface between metal and bone, for example, the metal is recognized as a foreign material as a result of metal ions given off by the material or wear debris and this causes a capsulation process in which connective tissue (soft tissue) covers the material, the formation of a non-crystal phase termed an amorphous phase or induces osteolysis due to the abrasive wear debris.

The biocompatible material has the same function as an in vivo biomaterial since it does not produce capsulation, protein attachment or thrombotic formation as referred to above. In particular, when disposed on the contact surface of the acetabular cup and/or the femoral head of a joint prosthesis; it is possible to prevent wear of the living bone. Furthermore abrasive wear debris from the biocompatible material produced as a result of sliding of the femoral head and the acetabular cup does not tend to produce a reaction with biological substances in the body and as a result, does not tend to result in osteolysis.

The biocompatible material includes polymer materials having phosphorylcholine groups. The polymer materials preferably include 2-methacryloyloxyethyl phosphorylcholine, 2-acryloyloxyethyl phosphorylcholine, 4-methacryloyloxybutyl phosphorylcholine, 6-methacryloyloxyhexyl phosphorylcholine, 6)-methacryloyloxyethylene phosphorylcholine and 4-styryloxybutyl phosphorylcholine.

Other examples of a biocompatible material include for example 2-methacryloyloxyethyl-2'-(trimethylammonio) ethyl phosphate, 3-methacryloyloxypropyl-2'-(trimethylammonio) ethyl phosphate, 4-methacryloyloxybutyl-2'-(trimethylammonio) ethyl phosphate, 5-methacryloyloxypentyl-2'-(trimethylammonio) ethyl phosphate, 6-methacryloyloxyhexyl-2'-(trimethylammonio) ethyl phosphate, 2-methacryloyloxyethyl-2'-(triethylammonio) ethyl phosphate, 2-methacryloyloxyethyl-2'-(tripropylammonio) ethyl phosphate, 2-methacryloyloxyethyl-2'-(tributylammonio) ethyl phosphate, 2-methacryloyloxypropyl-2'-(trimethylammonio) ethyl phosphate, 2-methacryloyloxybutyl-2'-(trimethylammonio) ethyl phosphate, 2-methacryloyloxypentyl-2'-(trimethylammonio) ethyl phosphate, 2-methacryloyloxyhexyl-2'-(trimethylammonio) ethyl phosphate, 2-methacryloyloxyethyl-3'-(trimethylammonio) propyl phosphate, 3-methacryloyloxypropyl-3'-(trimethylammonio) propyl phosphate, 4-methacryloyloxybutyl-3'-(trimethylammonio) propyl phosphate, 5-methacryloyloxypentyl-3'-(trimethylammonio) propyl phosphate, 6-methacryloyloxyhexyl-3'-(trimethylammonio) propyl phosphate, 2-methacryloyloxyethyl-4'-(trimethylammonio) butyl phosphate, 3-methacryloyloxypropy-4'-(trimethylammonio) butyl phosphate, 4-methacryloyloxybutyl-4'-(trimethylammonio) butyl phosphate, 5-methacryloyloxypentyl-4'-(trimethylammonio) butyl phosphate, and 6-methacryloyloxyhexyl-4'-(trimethylammonio) butyl phosphate.

In the biocompatible material layer, it is preferred that the polymer containing phosphorylcholine groups is covalently bonded as a graft polymer chain. By grafting the polymer in such a way, a biocompatible material layer having a predetermined thickness can be formed. In order to graft the polymer, a radical may be generated on the substrate by irradiation with energy radiation such as electron radiation, gamma-ray radiation or UV radiation, or heating. In particular, new function can be efficiently imparted by using UV radiation and a photo-polymerization agent without impairing characteristics of the substrate.

The thickness of the biocompatible material layer is preferably from 10 to 200 nm, and particularly preferably from 100 to 200 nm. Adhesion of the substrate can be suppressed by adjusting to the thickness in the above range.

Regarding wettability of the biocompatible material layer to water, the contact angle is preferably 30° or less. When the contact angle is 30° or less, in the case of using a total joint replacement, lubricity of the artificial joint is enhanced and production of abrasive wear debris is suppressed over a long period, thus making it possible to suppress loosening and to obtain a total joint replacement which requires small number of revision surgeries or required no revision surgery. In the case of using, as an artificial femoral head, in combination with a natural articular cartilage, damage of the natural articular cartilage can be suppressed.

The concentration of phosphorus atoms of the sliding surface of the biocompatible material layer is preferably 4 atomic % or more. Furthermore, both the concentration of phosphorus atoms and the concentration of nitrogen atoms of the sliding surface of the biocompatible material layer is preferably are preferably 4.6 atomic % or more. In the case of using as the total joint replacement, lubricity of the artificial joint is enhanced and production of abrasive wear debris is suppressed over a long period, thus making it possible to suppress loosening and to obtain a total joint replacement which requires small number of revision surgeries or required no revision surgery. Furthermore, in the case of using in combination with CLPE grafted with an MPC polymer or a Co—Cr alloy (in the case of using MPC graft polymer face-MPC graft polymer face in combination) a friction coefficient is extremely low and thus an artificial joint with extremely long lifetime can be achieved. In the case of using, as an artificial femoral head, in combination with a natural articular cartilage, damage of the natural articular cartilage can be suppressed. It is also possible to exert, as the biocompatible material, a function of the biomaterial in vivo without causing encapsulation, protein adsorption and thrombus formation. Phosphorus atoms of the sliding surface of the biocompatible material layer were measured by X-ray photoelectron spectroscopy.

Substrate

Metals constituting the substrate include titanium (Ti) and chromium (Cr), which have property to easily form hydroxyl groups. Alloys constituting the substrate include SUS alloys, Cr alloys and titanium alloys. Preferred examples of Cr alloys include Co—Cr alloys or Co—Cr—Mo alloys. Preferred examples of titanium alloys include Ti-6Al-4V alloy, Ti-15Mo-5Zr-3Al alloy, Ti-6Al-7Nb alloy, Ti-6Al-2Nb-1Ta alloy, Ti-15Zr-4Nb-4Ta alloy, Ti-15Mo-5Zr-3Al alloy, Ti-13Nb-13Zr alloy, Ti-12Mo-6Zr-2Fe alloy, Ti-15Mo alloy and Ti-6Al-2Nb-1Ta-0.8Mo alloy. Ceramics constituting the substrate include alumina, zirconia and titania, which are metal oxides capable of forming hydroxyl groups. These materials form oxides on the surface with plasma treatment and facilitate formation of hydroxyl groups. Thus these materials are preferably employed since the substrate and the binder layer are strongly bound by chemical bonds between their hydroxyl groups and the carboxyl groups of the binder layer. However any material may be employed as the substrate, as long as it has the property to form functional groups which can react with carboxyl groups of the binder layer formed on the substrate. The functional groups which can react with carboxyl group of the binder layer formed on the substrate are preferably hydroxyl groups. However they are not limited to the hydroxyl groups.

Only by subjecting alloys such as Ni—Cr alloys, Co—Cr alloys, stainless steel and titanium alloys to alumina sandblasting, an oxide film is naturally formed on the surface to obtain higher bond strength. In particular, the silicon alkoxide exhibits high bonding properties to chromium hydroxide formed from chromium oxide contained in alloys such as Ni—Cr alloys and Co—Cr alloys (Production Method)

The method of producing a sliding member according to present Embodiment 1 will be schematically described below.

First, a substrate 1 formed from metals, alloys, semiconductors or ceramics is subjected to ultrasonic cleaning with a solvent. Acetone, methanol and ethanol can be used as the solvent.

Subsequently, when Ni—Cr alloys, Co—Cr alloys or stainless steel are selected, the surface of the substrate may be subjected to a nitric acid treatment thereby increasing the chromium concentration on the substrate surface. Thus, it becomes possible to increase the concentration of Cr—OH formed on the substrate surface in the subsequent step and to improve bonding properties of the substrate 1 with the binder layer 3.

The substrate 1 subjected to the nitric acid treatment is placed in a plasma treatment device and subjected to an oxygen plasma treatment for 2 to 10 minutes to form an oxide on the surface of the substrate 1, and then a layer (Cr—OH) of a high-density hydroxide is formed. By treating in such a way, the surface of the substrate 1 is converted into a surface treated layer 2.

Subsequently, a silicon alkoxide is dissolved in an organic solvent containing a photo-polymerization initiator added therein and then the substrate 1 is immersed in the thus obtained solution. Methanol and ethanol can be used as the organic solvent. The concentration of the silicon alkoxide is preferably from 0.1% by weight to 10% by weight, and more preferably from 2% by weight to 5% by weight. Furthermore, IRGACURE (D2959), IRGACURE (D369) or benzophenone are preferably used as the photo-polymerization initiator and, of these, IRGACURE (D2959) is most preferred.

The thus coated substrate is under a normal pressure. The temperature is preferably from 40° C. to 120° C., and more preferably 70° C. to 120° C. The drying time is from 0.5 hour to 3 hours, and more preferably from 1 hour to 3 hours.

Furthermore, the biocompatible material monomer is dissolved in a solution containing the solvent dissolved therein. The biocompatible material monomer is preferably a substance containing at least one selected from 2-methacryloyloxyethylphosphorylcholine, 2-acryloyloxyethylphosphorylcholine, 4-methacryloyloxybutylphosphorylcholine, 6-methacryloyloxyhexylphosphorylcholine, ω-methacryloyloxyethylenephosphorylcholine, 4-styryloxybutylphosphorylcholine, 3-methacryloyloxypropyl-2'-(trimethylammonio)ethyl phosphate, 5-methacryloyloxypentyl-2'-(trimethylammonio)ethyl phosphate, 2-methacryloyloxyethyl-2'-(triethylammonio)ethyl phosphate, 2-methacryloyloxyethyl-2'-(tripropylammonio)ethyl phosphate, 2-methacryloyloxyethyl-2'-(tributylammonio)ethyl phosphate, 2-methacryloyloxybutyl-2'-(trimethylammonio)ethyl phosphate, 2-methacryloyloxypentyl-2'-(trimethylammonio)ethyl phosphate, 2-methacryloyloxyhexyl-2'-(trimethylammonio)ethyl phosphate, 2-methacryloyloxyethyl-3'-(trimethylammonio)propyl phosphate, 3-methacryloyloxypropyl-3'-(trimethylammonio)propyl phosphate, 4-methacryloyloxybutyl-3'-(trimethylammonio)propyl phosphate, 5-methacryloyloxypentyl-3'-(trimethylammonio)propyl phosphate, 6-methacryloyloxyhexyl-3'-(trimethylammonio)propyl phosphate, 2-methacryloyloxyethyl-4'-(trimethylammonio)butyl phosphate, 3-methacryloyloxypropyl-4'-(trimethylammonio)butyl phosphate, 4-methacryloyloxybutyl-4'-(trimethylammonio)butyl phosphate, 5-methacryloyloxypentyl-4'-(trimethylammonio)butyl phosphate and 6-methacryloyloxyhexyl-4'-(trimethylammonio)butyl phosphate, and more preferably MPC. The solvent is preferably water. The water may contain ethanol.

Subsequently, the substrate is polymerized by photo-irradiation to form a biocompatible material layer 4. Proper wavelength of UV is from 300 nm to 400 nm. The concentration of the monomer is from 0.25 to 1.00 mol/L, and more preferably from 0.50 to 1.00 mol/L. The polymerization temperature is preferably from 20° C. to 80° C., and more preferably about 60° C. The photo-irradiation time is preferably from 20 minutes to 180 minutes, and more preferably from 45 minutes to 90 minutes.

After the polymerization, the substrate is washed by immersing in water or an organic solvent. Methanol, ethanol and isopropyl alcohol can be used as the organic solvent, and ethanol is most preferred.

Embodiment 2

Figure 2:
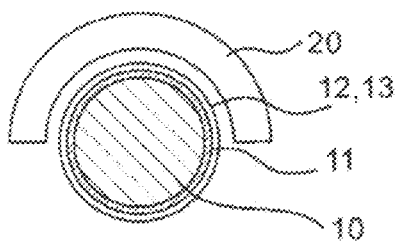
FIG. 2 is a schematic sectional view of a femoral head of an artificial joint according to a first embodiment of the present invention.

FIG. 2 is a cross-sectional view of a joint prosthesis manufactured by the production method of the present invention. As shown in FIG. 2, the joint prosthesis according to the second embodiment of the present invention comprises a femoral head 10 made of metal, alloy or ceramic and an acetabular cup 20 made of organic material. The femoral head 10 has a surface processed layer 11 on at least one section of the femoral head 10. The surface processed layer 11 is formed by processing at least one section of the surface of the femoral head 10. The femoral head 10 has a binder layer 12 laminated on the surface processed layer 11 and a biocompatible material layer 13 laminated on the binder layer 12. The femoral head 10 made of metal, alloy or ceramic in a joint prosthesis according to the second embodiment of the present invention is coated with a biocompatible material layer 13 via the binder layer 12 and the surface processed layer 11 and therefore does not produce wear debris of for example, metal. Moreover even when wear debris is produced from the biocompatible material layer 13 coating the femoral head 10, the wear debris from the biocompatible material layer does not have an adverse effect on the human body. Therefore a joint prosthesis according to the second embodiment can be preferably employed.

Embodiment 3

Figure 3:
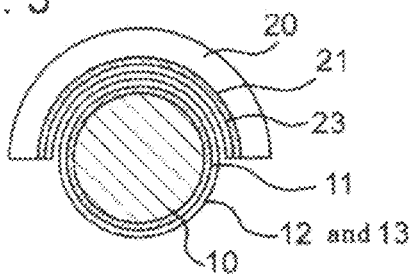
FIG. 3 is a schematic sectional view of a femoral head of an artificial joint according to a second embodiment of the present invention.

As shown in FIG. 3, a joint prosthesis according to the third embodiment of the present invention comprises a femoral head 10 made of metal, alloy or ceramic and an acetabular cup 20 made of organic material. The femoral head 10 and the acetabular cup 20 have a surface-treated layer 11, 21 on at least one section thereof respectively. The surface-treated layer 11 is formed by treatment at least one section of the surface of the femoral head 10 or the acetabular cup 20. The femoral head 10 has a binder layer 12 laminated on the surface-treated layer 11 and a biocompatible material layer 13 laminated on the binder layer 12. These biocompatible material layers 13 are placed in contact.

The acetabular cup 20 is prepared by known methods (disclosed in, for example, Japanese Unexamined Patent Publication (Kokai) No. 2003-310649) in which the acetabular cup 20 is immersed in an acetone solution containing benzophenone, and then is immersed in an aqueous solution containing a biocompatible material after drying, a biocompatible material layer 23 is formed by UV irradiating at a wavelength of 300 to 400 nm.

In contrast to the joint prosthesis according to the second embodiment, a joint prosthesis according to the third embodiment has a biocompatible material layer 23 formed on the surface of the acetabular cup 20 whereas in the joint prosthesis according to the second embodiment, there is no surface processed layer or the like formed on the surface of the acetabular cup 20. Therefore the third embodiment differs from the second embodiment. The surface of the acetabular cup 20 made of an organic material in the joint prosthesis according to the third embodiment is coated with a biocompatible material layer 23 and wear debris is not produced from the acetabular cup 20 made of organic material, resulting in solving the problem of loosening. Therefore, it can be preferably employed.

Embodiment 4

Figure 4:
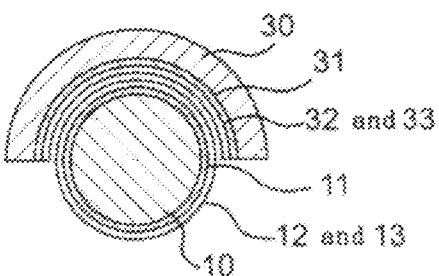
FIG. 4 is a schematic sectional view of a femoral head of an artificial joint according to a third embodiment of the present invention.
Figure 5:
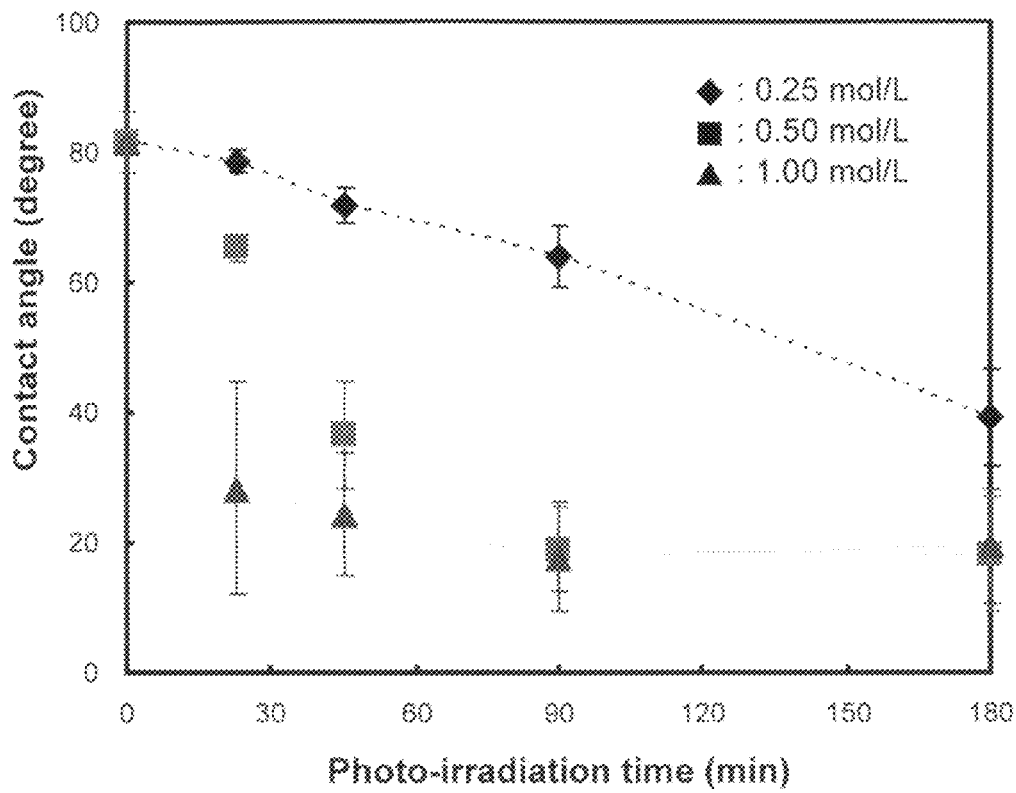
FIG. 5 is a graph showing the magnitude of a contact angle versus a photo-irradiation time with respect to an MPC polymer membrane according to Example 1.
Figure 6:
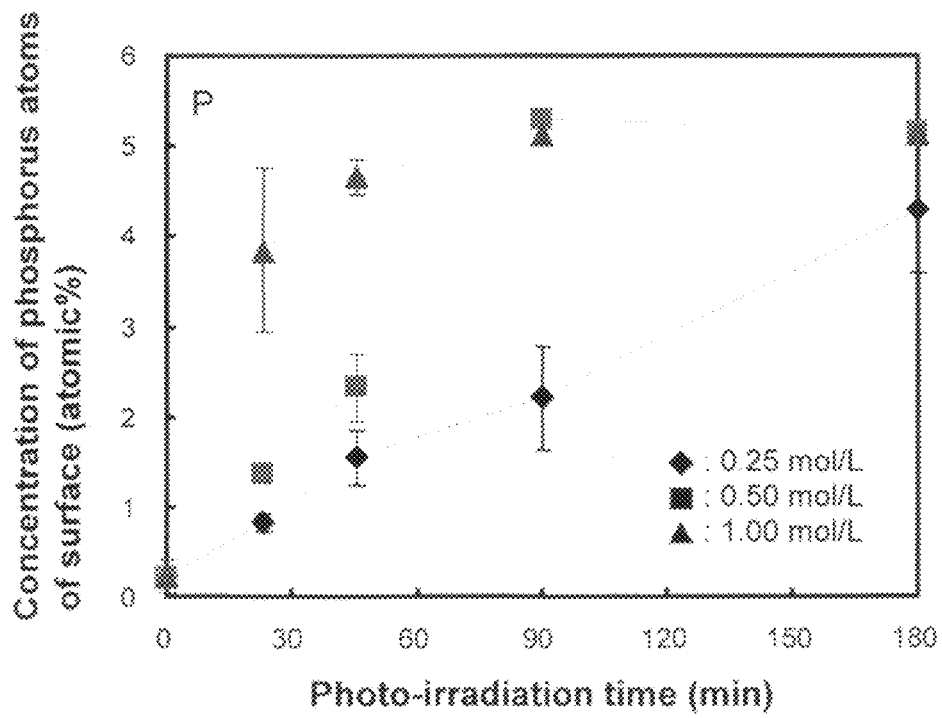
FIG. 6 is a graph showing the concentration of phosphorus atoms versus a photo-irradiation time with respect to an MPC polymer membrane according to Example 1.

As shown in FIG. 4, the joint prosthesis according to the fourth embodiment of the present invention comprises a femoral head 10 made of metal, alloy or ceramic and an acetabular cup 30 made of metal, alloy or ceramic. The femoral head 10 and the acetabular cup 30 have a surface-treated layer 11, 31 on at least one section thereof respectively. The surface-treated layer 11, 31 is formed by treatment at least one section of the surface of the femoral head 10 or the acetabular cup 30. The femoral head 10 and the acetabular cup 30 have a binder layer 12, 32 laminated on the surface-treated layer 11, 31 and a biocompatible material layer 13, 33 laminated on the binder layer 12, 32. These biocompatible material layers 13, 33 are placed in contact.

In the joint prosthesis according to the fourth embodiment, it has an acetabular cup made of metal, alloy or ceramic whereas in the joint prosthesis according to the third embodiment, the acetabular cup is made of organic material and therefore it differs from the joint prosthesis according to the second embodiment. A joint prosthesis according to the fourth embodiment has an acetabular cup made of metal, alloy or ceramic and therefore can be preferably employed due to its superior hardness compared to components made of organic material.

In the artificial joint according to the present invention, particularly, the artificial hip joint, a femoral head of a femur and an acetabular cup are preferably formed from combinations of materials shown in Table 1.

For example, it is preferred that the femoral head includes a substrate formed from a Co—Cr alloy, an MPS graft polymerized biocompatible material layer laminated on the sliding surface of the substrate, and a binder layer formed from silica, which enables bonding of the substrate with the biocompatible material layer, while the acetabular cup includes a hemispheric substrate formed from a Co—Cr alloy.

In another aspect, the femoral head includes a substrate formed from a Co—Cr alloy, while
the acetabular cup includes a hemispheric substrate formed from a Co—Cr alloy, a MPC graft polymerized biocompatible material layer laminated on the sliding surface of the substrate, and a binder layer formed from silica, which enables bonding of the substrate with the biocompatible material layer.

In still another aspect, the femoral head includes a substrate formed from a Co—Cr alloy, an MPC graft polymerized biocompatible material layer laminated on the sliding surface of the substrate, and a binder layer formed from silica, which enables bonding of the substrate with the biocompatible material layer, while the acetabular cup includes a hemispheric substrate formed from a Co—Cr alloy, an MPC graft polymerized biocompatible material layer laminated on the sliding surface of the substrate, and a binder layer formed from silica, which enables bonding of the substrate with the biocompatible material layer.

In a further aspect, the femoral head includes a substrate formed from ceramics, an MPC graft polymerized biocompatible material layer laminated on the sliding surface of the substrate, and a binder layer formed from silica, which enables bonding of the substrate with the biocompatible material layer, while the acetabular cup includes a hemispheric substrate formed from ceramics.

In a further aspect, femoral head includes a substrate formed from ceramics, while the acetabular cup includes a hemispheric substrate formed from ceramics, an MPC graft polymerized biocompatible material layer laminated on the sliding surface of the substrate, and a binder layer formed from silica, which enables bonding of the substrate with the biocompatible material layer.

In a further aspect, femoral head includes a substrate formed from ceramics, an MPC graft polymerized biocompatible material layer laminated on the sliding surface of the substrate, and a binder layer formed from silica, which enables bonding of the substrate with the biocompatible material layer, while the acetabular cup includes a hemispheric substrate formed from ceramics, an MPC graft polymerized biocompatible material layer laminated on the sliding surface of the substrate, and a binder layer formed from silica, which enables bonding of the substrate with the biocompatible material layer.

In a further aspect, the femoral head includes a substrate formed from a Co—Cr alloy, an MPC graft polymerized biocompatible material layer laminated on the sliding surface of the substrate, and a binder layer formed from silica, which enables bonding of the substrate with the biocompatible material layer, while the acetabular cup includes a hemispheric substrate formed from ceramics.

In a further aspect, the femoral head includes a substrate formed from ceramics, while the acetabular cup includes a hemispheric substrate formed from a Co—Cr alloy, an MPC graft polymerized biocompatible material layer laminated on the sliding surface of the substrate, and a binder layer formed from silica, which enables bonding of the substrate with the biocompatible material layer.

In a further aspect, the femoral head includes a substrate formed from ceramics, an MPC graft polymerized biocompatible material layer laminated on the sliding surface of the substrate, and a binder layer formed from silica, which enables bonding of the substrate with the biocompatible material layer, while the acetabular cup includes a hemispheric substrate formed from a Co—Cr alloy.

In a further aspect, the femoral head includes a substrate formed from a Co—Cr alloy, while the acetabular cup includes a hemispheric substrate formed from ceramics, an MPC graft polymerized biocompatible material layer laminated on the sliding surface of the substrate, and a binder layer formed from silica, which enables bonding of the substrate with the biocompatible material layer.

In a further aspect, the femoral head includes a substrate formed from a Co—Cr alloy, an MPC graft polymerized biocompatible material layer laminated on the sliding surface of the substrate, and a binder layer formed from silica, which enables bonding of the substrate with the biocompatible material layer, while the acetabular cup includes a hemispheric substrate formed from ceramics, an MPC graft polymerized biocompatible material layer laminated on the sliding surface of the substrate, and a binder layer formed from silica, which enables bonding of the substrate with the biocompatible material layer.

In a further aspect, the femoral head includes a substrate formed from ceramics, an MPC graft polymerized biocompatible material layer laminated on the sliding surface of the substrate, and a binder layer formed from silica, which enables bonding of the substrate with the biocompatible material layer, while the acetabular cup includes a hemispheric substrate formed from a Co—Cr alloy, an MPC graft polymerized biocompatible material layer laminated on the sliding surface of the substrate, and a binder layer formed from silica, which enables bonding of the substrate with the biocompatible material layer.

In a further aspect, the femoral head includes a substrate formed from a Co—Cr alloy, an MPC graft polymerized biocompatible material layer laminated on the sliding surface of the substrate, and a binder layer formed from silica, which enables bonding of the substrate with the biocompatible material layer, while the acetabular cup includes a hemispheric substrate formed from polyethylene.

In a further aspect, the femoral head includes a substrate formed from ceramics, an MPC graft polymerized biocompatible material layer laminated on the sliding surface of the substrate, and a binder layer formed from silica, which enables bonding of the substrate with the biocompatible material layer, while the acetabular cup includes a hemispheric substrate formed from polyethylene.

In a further aspect, the femoral head includes a substrate formed from a Co—Cr alloy, an MPC graft polymerized biocompatible material layer laminated on the sliding surface of the substrate, and a binder layer formed from silica, which enables bonding of the substrate with the biocompatible material layer, while the acetabular cup includes a hemispheric substrate formed from polyethylene, an MPC graft polymerized biocompatible material layer laminated on the sliding surface of the substrate, and a binder layer formed from silica, which enables bonding of the substrate with the biocompatible material layer.

In a further aspect, the femoral head includes a substrate formed from ceramics, an MPC graft polymerized biocompatible material layer laminated on the sliding surface of the substrate, and a binder layer formed from silica, which enables bonding of the substrate with the biocompatible material layer, while the acetabular cup includes a hemispheric substrate formed from polyethylene, an MPC graft polymerized biocompatible material layer laminated on the sliding surface of the substrate, and a binder layer formed from silica, which enables bonding of the substrate with the biocompatible material layer.

TABLE 1

| Combinations | Femoral heads of femur | Acetabular cups |
| --- | --- | --- |
| 1 | Co—Cr alloy grafted with MPC polymer | Co—Cr alloy |
| 2 | Co—Cr alloy | Co—Cr alloy grafted with MPC polymer |

TABLE 1-continued

| Combinations | Femoral heads of femur | Acetabular cups |
|---|---|---|
| 3 | Co—Cr alloy grafted with MPC polymer | Co—Cr alloy grafted with MPC polymer |
| 4 | Ceramics grafted with MPC polymer | Ceramics |
| 5 | Ceramics | Ceramics grafted with MPC polymer |
| 6 | Ceramics grafted with MPC polymer | Ceramics grafted with MPC polymer |
| 7 | Co—Cr alloy grafted with MPC polymer | Ceramics |
| 8 | Ceramics | Co—Cr alloy grafted with MPC polymer |
| 9 | Ceramics grafted with MPC polymer | Co—Cr alloy |
| 10 | Co—Cr alloy | Ceramics grafted with MPC polymer |
| 11 | Co—Cr alloy grafted with MPC polymer | Ceramics grafted with MPC polymer |
| 12 | Ceramics grafted with MPC polymer | Co—Cr alloy grafted with MPC polymer |
| 13 | Co—Cr alloy grafted with MPC polymer | Polyethylene |
| 14 | Ceramics grafted with MPC polymer | Polyethylene |
| 15 | Co—Cr alloy grafted with MPC polymer | Polyethylene grafted with MPC polymer |
| 16 | Ceramics grafted with MPC polymer | Polyethylene grafted with MPC polymer |

Example 1

The biomaterial according to the present invention was produced by the following and the resultant biomaterial was tested. A Co—Cr—Mo alloy with the composition of Co-28Cr-6Mo was used as the material of a substrate. Silica was used as the material of a binder layer and MPC was used as a biocompatible material.

1) First a sample of a Co—Cr—Mo alloy (composition: Co-28Cr-6Mo alloy) was subjected to ultrasonic cleaning in an acetone solution.

(2) Then, the sample was subjected to a high Cr treatment (nitric acid treatment) by immersing in a 20 to 40% nitric acid for 30 minutes.

(3) The sample subjected to the nitric acid treatment was placed in a plasma treatment device, subjected to an oxygen plasma treatment for 5 minutes to form an oxide on the surface of the sample, and then a high-density Cr—OH was formed.

(4) The treated surface of the sample was quickly immersed in a mixed solution of 5 wt % methacryloyloxypropyltrimethoxysilane/0.1 wt % IRGACURE (D2959)/93.9% by weight ethanol (anhydrate)/0.1 wt % succinic acid ethanol (95) solution.

(5) The sample was subjected to a heat treatment at 70° C., for 3 hours (under a normal pressure).

(6) The sample was immersed in 0.25 to 1.00 mol/L of an aqueous MPC solution and then irradiated with 350 nm UV radiation at 60° C. for 23 minutes to 180 minutes.

(7) After formation of the MPC polymer, the sample was washed by immersing overnight in ethanol.

(Measurements of Hydrophilicity, Concentration of Phopshorus Atoms, and Thickness)

With respect to an MPC polymer membrane of each sample, measurements of a contact angle with water (indicator of hydrophilicity) and the concentration of phosphorus atoms as well as observation using a transmission electron microscope (TEM) were conducted. The results are shown in FIG. 5 to FIG. 10.

With respect to plural samples in which the monomer concentration and the irradiation time of UV radiation were changed, a contact angle with water of a MPC polymer membrane (indicator of hydrophilicity) was measured. The results are summarized in FIG. 5. As is apparent from FIG. 5, the contact angle tends to decrease as the irradiation time of UV radiation increased in any monomer concentration. When the monomer concentration is 0.50 mol/L, the sample showed a small contact angle of about 36° at the irradiation time of 45 minutes, or 19° at 90 minutes. When the monomer concentration is 1.00 mol/L, the sample showed a small contact angle of about 28° at the irradiation time of 23 minutes, or 18° at 90 minutes.

With respect to plural samples in which the monomer concentration and the UV irradiation time were changed, XPS analysis was conducted and the concentration of phosphorus atoms was measured. The results are summarized in FIG. 6. As is apparent from FIG. 6, the concentration of phosphorus atoms is the highest when the monomer concentration is 0.5 mol/L and the irradiation time is 90 minutes, and was identical to the theoretical value (the concentration of phosphorus atoms: 5.3 atomic %) of the MPC polymer. Within the range of satisfactory hydrophilicity, namely, the monomer concentration is 0.50 mol/L and the irradiation time is 90 minutes or more, and the monomer concentration is 1.00 mol/L and the irradiation time is 23 minutes or more, the concentration of phosphorus atoms was 3.8 atomic % or more. In particular, when the monomer concentration is 0.50 mol/L and the irradiation time is 90 minutes or more, and the monomer concentration is 1.00 mol/L and the irradiation time is 45 minutes or more, the concentration of phosphorus atoms was 4.6 atomic % or more.

Figure 7:
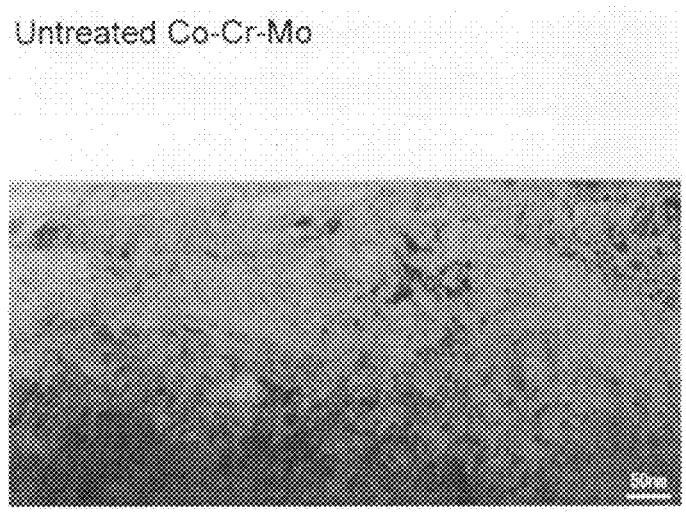
FIG. 7 is a TEM micrograph of a cross section of an untreated cobalt-chromium-molybdenum (hereinafter referred to as "Co—Cr—Mo") alloy.
Figure 8:
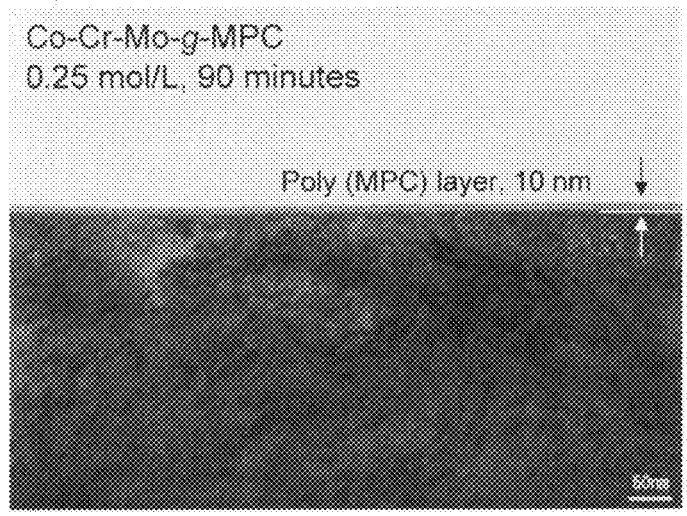
FIG. 8 is a TEM micrograph of a cross section of a Co—Cr—Mo alloy surface-treated with 0.25 mol/L of an aqueous MPC solution for 90 minutes.
Figure 9:
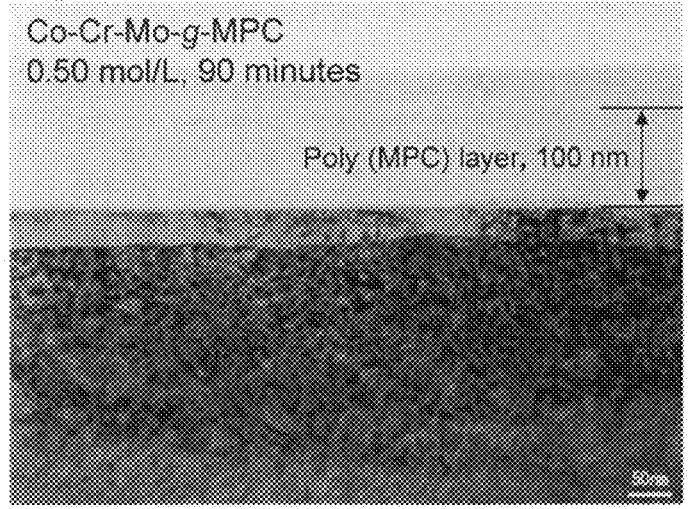
FIG. 9 is a TEM micrograph of a cross section of a Co—Cr—Mo alloy surface-treated with 0.50 mol/L of an aqueous MPC solution for 90 minutes.
Figure 10:
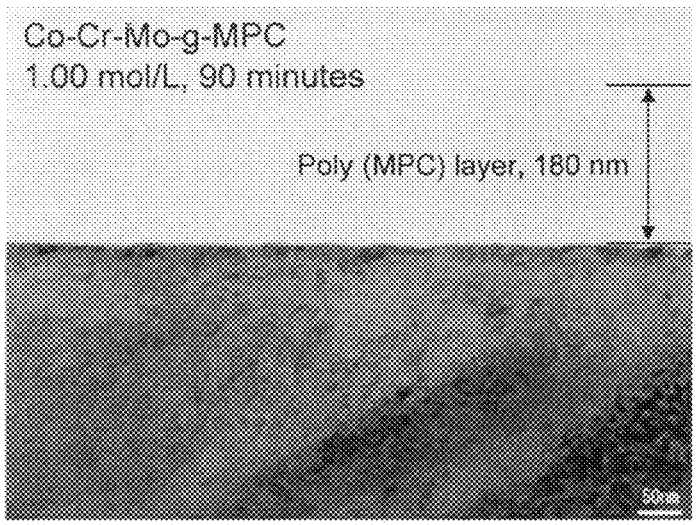
FIG. 10 is a TEM micrograph of a cross section of a Co—Cr—Mo alloy surface-treated with 1.00 mol/L of an aqueous MPC solution for 90 minutes.

With respect to plural samples in which the monomer concentration and the irradiation time of UV radiation were changed, the thickness of an MPC polymer membrane, with which a Co—Cr—Mo alloy is coated, was measured. Using transmission electron microscope (TEM), Model HF-2000, manufactured by Hitachi, Ltd., observation was conducted at an acceleration voltage of 200 kV. FIG. 7 shows a sample which is not coated with MPC, FIG. 8 shows a sample produced under the conditions of the monomer concentration of 0.25 mol/L, FIG. 9 shows a sample produced under the conditions of the monomer concentration of 0.50 mol/L, FIG. 10 shows a sample produced under the conditions of the monomer concentration of 1.00 mol/L, respectively. In all samples, the UV irradiation time is 90 minutes. In FIG. 8 to FIG. 10, a coating layer (an MPC polymer membrane), which is not observed in FIG. 7, was observed. The thickness was 10 nm in FIG. 8, the thickness was 100 nm in FIG. 9, and the thickness was 180 nm in FIG. 10. TEM images at plural positions were observed. As a result, it was recognized that the entire Co—Cr—Mo alloy is coated with an MPC polymer membrane.

Example 2

The biomaterial according to the present invention was produced by the following and the resultant biomaterial was tested. A Co—Cr—Mo alloy with the composition of Co-28Cr-6Mo was used as the material of a substrate. Silica was used as the material of a binder layer and MPC was used as a biocompatible material.

1) First a sample of a Co—Cr—Mo alloy (composition: Co-28Cr-6Mo alloy) was subjected to ultrasonic cleaning in an acetone solution.

(2) Then, the sample was subjected to a high Cr treatment (nitric acid treatment) by immersing in a 20 to 40% nitric acid for 30 minutes.

(3) The sample subjected to the nitric acid treatment was placed in a plasma treatment device, subjected to an oxygen plasma treatment for 5 minutes to form an oxide on the surface of the sample, and then a high-density Cr—OH was formed.

(4) The treated surface of the sample was quickly immersed in a mixed solution of 5 wt % methacryloyloxypropyltrimethoxysilane/0.1 wt % IRGACURE (D2959)/93.9% by weight ethanol (anhydrate)/0.1 wt % succinic acid ethanol (95) solution.

(5) The sample was subjected to a heat treatment at 70° C., for 3 hours (under a normal pressure).

(6) The sample was immersed in 0.50 mol/L of an aqueous MPC solution and then irradiated with 350 nm UV radiation at 60° C. for 90 minutes.

(7) After formation of the MPC polymer, the sample was washed by immersing overnight in ethanol.

(Measurement of Friction Coefficient)

Figure 11:
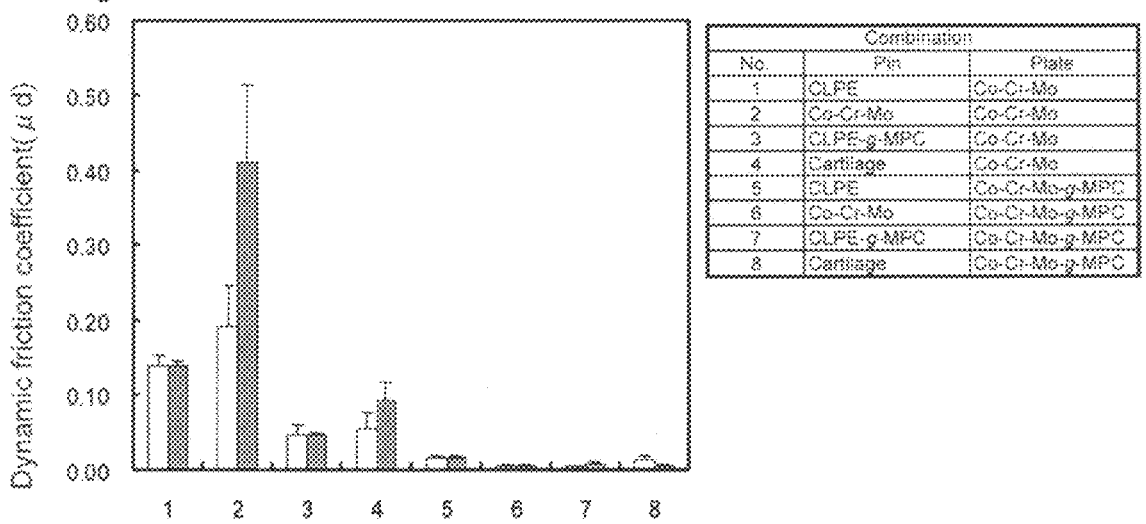
FIG. 11 is a graph showing a friction coefficient measured by a ball-on-flat type friction tester with respect to an MPC polymer membrane according to Example 2.

With respect to an MPC polymer membrane of each sample, a friction coefficient. The results are shown in FIG. 11.

The friction coefficient decreased to ⅕ to 1/40 by using a Co—Cr—Mo alloy plate grafted with an MPC polymer (comparison of combinations 1 to 4 with those of 5 to 8).

Characteristics of the cartilage can be maintained by using a Co—Cr—Mo alloy plate grafted with an MPC polymer (comparison of combination 4 with that of 8).

By using a Co—Cr—Mo alloy plate grafted with an MPC polymer, the friction coefficient is extremely low when (in the prior art Co—Cr—Mo alloy grafted with an MPC polymer via 4-META, since an MPC polymer membrane had a low density, the friction coefficient increased when used in combination with an MPC graft polymer face-MPC graft polymer face (refer to documents: Kyomoto M, et al.: High lubricious surface of cobalt-chromium-molybdenum alloy prepared by grafting poly(2-methacryloyloxyethyl phosphorylcholine; and Biomaterials 28: 3121-3130, 2007).

Example 3

The biomaterial according to the present invention was produced by the following and the resultant biomaterial was tested. A Co—Cr—Mo alloy with the composition of Co-28Cr-6Mo was used as the material of a substrate. Silica was used as the material of a binder layer and MPC was used as a biocompatible material.

1) First a sample of a Co—Cr—Mo alloy (composition: Co-28Cr-6Mo alloy) was subjected to ultrasonic cleaning in an acetone solution.

(2) Then, the sample was subjected to a high Cr treatment (nitric acid treatment) by immersing in a 20 to 40% nitric acid for 30 minutes.

(3) The sample subjected to the nitric acid treatment was placed in a plasma treatment device, subjected to an oxygen plasma treatment for 5 minutes to form an oxide on the surface of the sample, and then a high-density Cr—OH was formed.

(4) The treated surface of the sample was quickly immersed in a mixed solution of 5 wt % methacryloyloxypropyltrimethoxysilane/0.1 wt % IRGACURE (D2959)/93.9% by weight ethanol (anhydrate)/0.1 wt % succinic acid ethanol (95) solution.

(5) The sample was subjected to a heat treatment at 70° C., for 3 hours (under a normal pressure).

(6) The sample was immersed in 0.50 mol/L of an aqueous MPC solution and then irradiated with 350 nm UV radiation at 60° C. for 90 minutes.

(7) After formation of the MPC polymer, the sample was washed by immersing overnight in ethanol.

(Evaluation of Amount of Adsorbed Protein)

Figure 12:
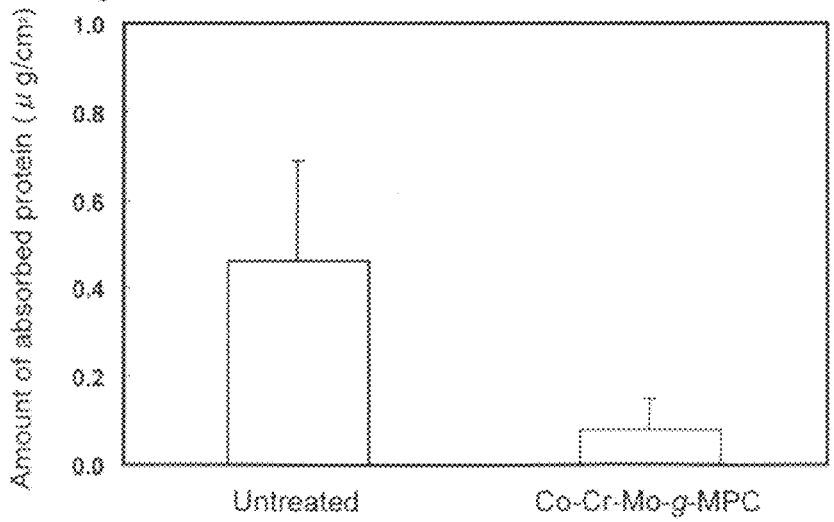
FIG. 12 is a graph showing an amount of adsorbed protein with respect to an MPC polymer membrane according to Example 3.
Figure 13:
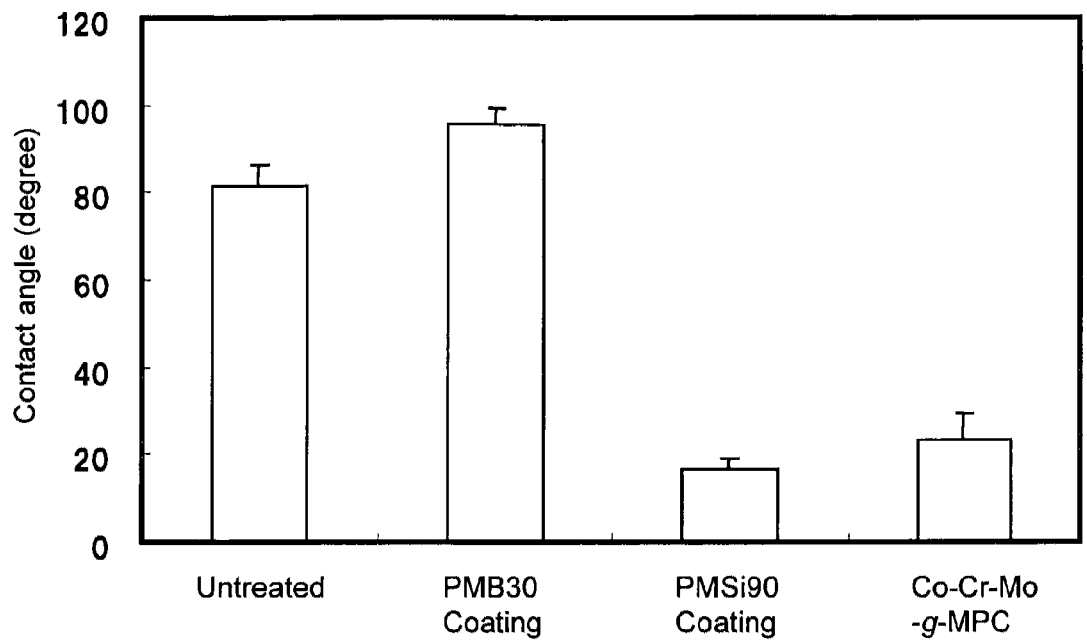
FIG. 13 is a graph showing a contact angle with water with respect to an MPC polymer membrane according to Example 4.
Figure 14:
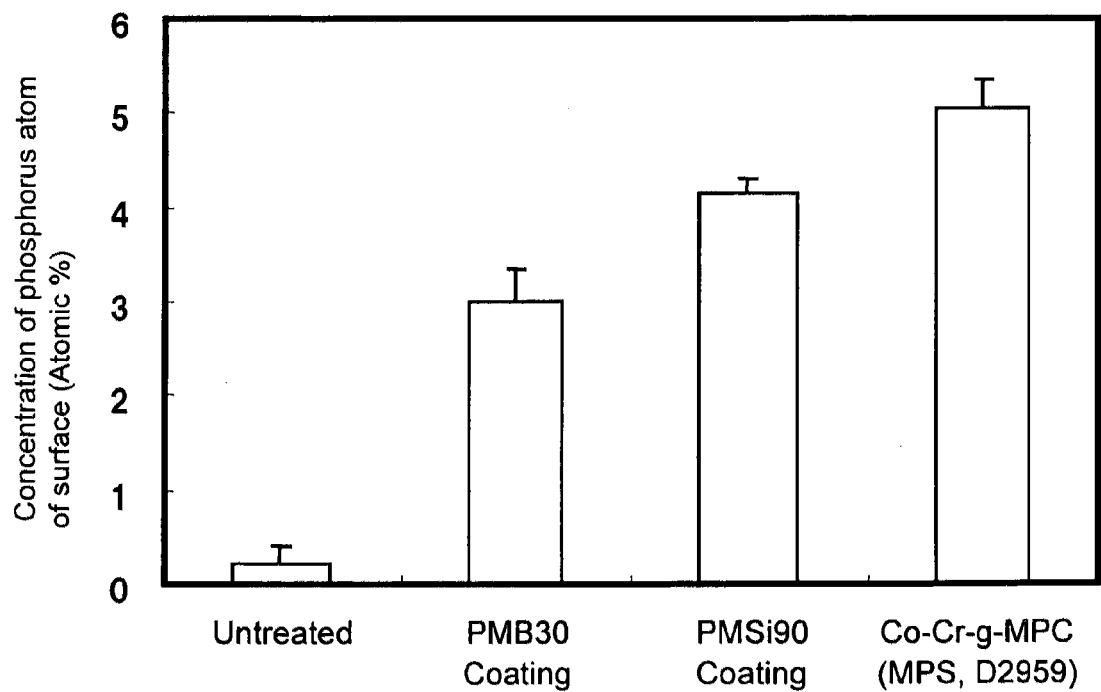
FIG. 14 is a graph showing the concentration of phosphorus atoms with respect to an MPC polymer membrane according to Example 4.
Figure 15:
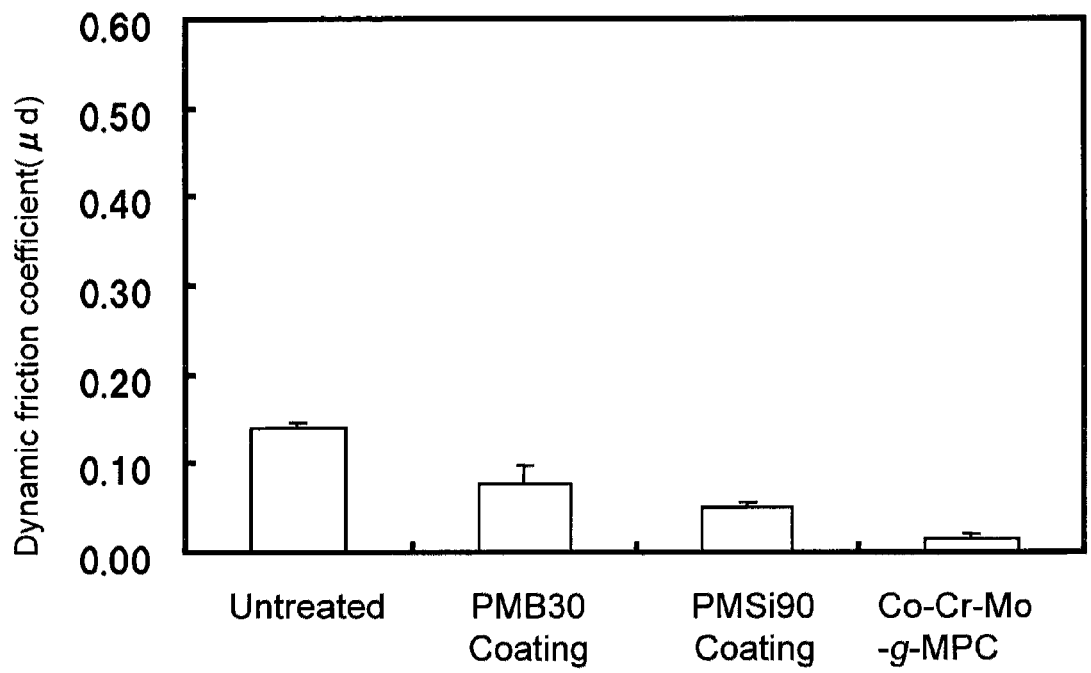
FIG. 15 is a graph showing a friction coefficient measured by a pin-on-flat type friction tester with respect to an MPC polymer membrane according to Example 4.
Figure 16:
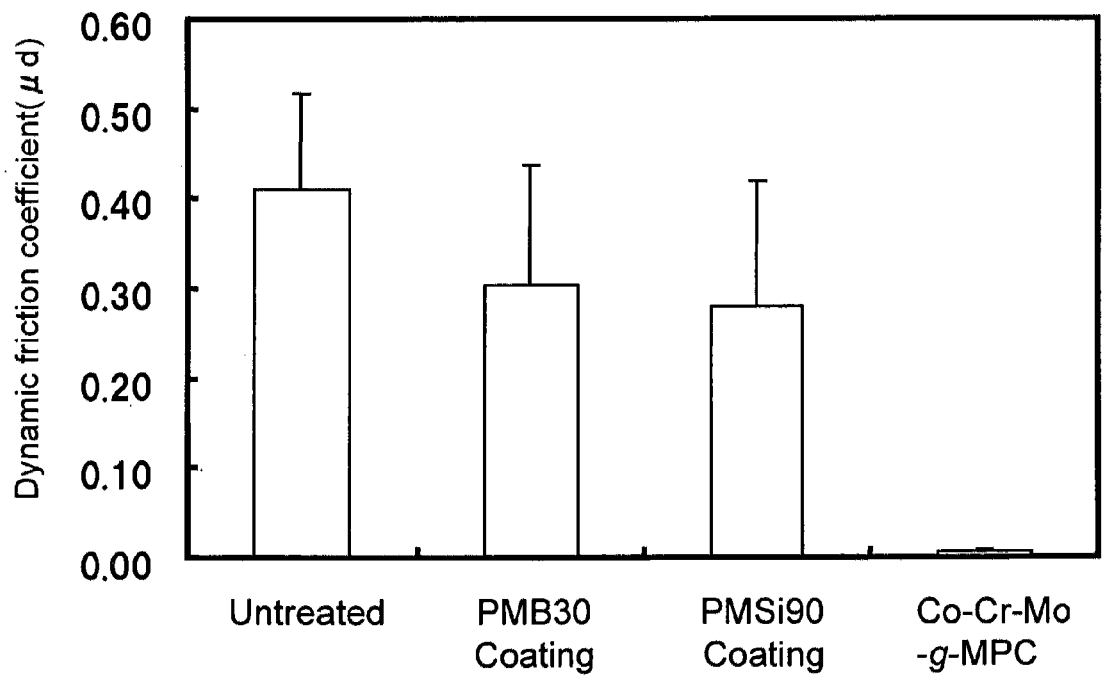
FIG. 16 is a graph showing a dynamic friction coefficient with respect to an MPC polymer membrane according to Example 4.

The amount of adsorbed protein of each sample was measured by a Micro BCA method. Bovine albumin serum was used as protein. The results are shown in FIG. 12. The untreated sample was compared with the sample produced under the conditions of the monomer concentration of 0.50 mol/L and the irradiation time of 90 minutes. As is apparent from FIG. 12, the amount of adsorbed protein of a Co—Cr—Mo alloy grafted with an MPC polymer was an extremely low value. It was the value which identical or lower than that of a conventionally reported value of the antithrombotic surface (refer to Non-Patent Document; Ishihara K, et al.: Hemocompatibility of human whole blood on polymers with a phospholipid polar group and its mechanism. J Biomed Mater Res 26: 1543-1552, 1992).

Example 4

The biomaterial according to the present invention (hereinafter simply referred to as "Co—Cr—Mo-g-MPC") was produced in the same manner as in Example 2 and the resultant biomaterial was tested. As a comparison, a Co—Cr—Mo alloy coated with a MPC copolymer formed from butyl methacrylate and MPC in a ratio of 30:70 (hereinafter simply referred to as "PMB30") or an MPC copolymer formed from methacryloyloxypropyltrimethoxysilane and MPC in a ratio of 10:90 (hereinafter simply referred to as "PMSi90") was prepared.

(Measurements of Hydrophilicity, Concentration of Phosphorus Atoms, and Friction Coefficient)

With an MPC polymer membrane of each sample, a contact angle (indicator of hydrophilicity), the concentration of phosphorus atoms, and a friction coefficient using a pin-on-flat type friction tester were measured. The results are shown in FIG. 13 to FIG. 16.

With respect to an MPC polymer membrane of each sample, a contact angle (indicator of hydrophilicity) with water of an MPC polymer membrane was measured. The results are summarized in FIG. 13. As is apparent from FIG. 13, the contact angle was low in PMSi90 coating (MPC of 90%) coated with PMSi90 having a high content of MPC in the coated MPC polymer membrane, or Co—Cr—Mo-g-MPC (MPC of 100%) coated with an MPC homopolymer.

With respect to an MPC polymer membrane of each sample, the concentration of phosphorus atoms was measured by XPS analysis. The results are summarized in FIG. 14. As is apparent from FIG. 14, the concentration of phosphorus atoms was highest in Co—Cr—Mo-g-MPC coated with an MPC homopolymer and was identical to the theoretical value (the concentration of phosphorus atoms of 5.3 atomic %) of an MPC homopolymer.

With respect to an MPC polymer membrane of each sample, a friction coefficient was measured by a pin-on-flat type friction tester. The results are summarized in FIGS. 15 to 16. The results obtained by using a combined pin formed from polyethylene are summarized in FIG. 15, and the results obtained by using a combined pin formed from Co—Cr—Mo alloy are summarized in FIG. 16. In the results of the friction coefficient, an MPC polymer is prepared by covalently bonding as a graft chain, and low friction was realized when the degree of freedom of molecules is high. When a Co—Cr—Mo alloy is used in combination with a Co—Cr—Mo-g-MPC, the friction coefficient was extremely low.

The invention claimed is:

1. A sliding member comprising:
a substrate capable of forming hydroxyl groups; and
a biocompatible material layer laminated on appropriate sections of the substrate,
wherein the hydroxyl groups are formed on at least a required section of a surface of the substrate by surface treating, and the biocompatible material layer is formed from a polymer containing phosphorylcholine groups,
wherein the substrate and the biocompatible material layer are joined via a binder layer formed from silica covalently bonded with the hydroxyl groups and the biocompatible material, and
wherein the silica comprises a photopolymerization initiator.

2. The sliding member according to claim 1, wherein the binder layer is formed through a dehydration-condensation reaction of at least one silicon alkoxide selected from the group of consisting of methacryloyloxypropyltrimethoxysilane, methacryloyloxypropylmethyldimethoxysilane, methacryloyloxypropyltriethoxysilane, and acryloyloxypropyltrimethoxysilane.

3. A prosthesis comprising the sliding member claimed in claim 2.

4. The sliding member according to claim 1, wherein the biocompatible material layer is formed from a polymer containing phosphorylcholine groups selected from the group consisting of a poly(2-methacryloyloxyethyl phosphorylcholine) and a copolymer containing 2-methacryloyloxyethyl phosphorylcholine.

5. The sliding member according to claim 4, wherein the biocompatible material layer is formed in such a manner that the polymer containing the phosphorylcholine groups is covalently bonded as a graft polymer chain.

6. A prosthesis comprising the sliding member claimed in claim 5.

7. A prosthesis comprising the sliding member claimed in claim 4.

8. The sliding member according to claim 1, wherein the substrate is formed from at least one material selected from the group consisting of titanium, a cobalt-chromium alloy, a cobalt-chromium-molybdenum alloy, a nickel-chromium alloy, stainless steel, a titanium base alloy, an alumina containing ceramic, a zirconia containing ceramic, and a titania containing ceramic.

9. A prosthesis comprising the sliding member claimed in claim 8.

10. The sliding member according to claim 1, wherein the substrate comprises a chromium component or a titanium component, and
wherein the chromium component or the titanium component at a surface of the substrate is oxidized by an oxygen plasma treatment to form the hydroxyl groups.

11. A prosthesis comprising the sliding member claimed in claim 10.

12. The sliding member according to claim 1, which is a hip joint prostheses, a shoulder joint prostheses, a vertebral prostheses, a knee joint prostheses, an elbow joint prostheses, an ankle joint prostheses, a finger joint prostheses, or an artificial disc, and
wherein the substrate is formed from a ceramic or a cobalt-chromium alloy.

13. A prosthesis comprising the sliding member claimed in claim 12.

14. A prosthesis comprising the sliding member claimed in claim 1.

15. A sliding member comprising:
a substrate capable of forming hydroxyl groups; and
a biocompatible material layer laminated on appropriate sections of the substrate,
wherein the hydroxyl groups are formed on at least a required section of a surface of the substrate by surface treating, and the biocompatible material layer is formed from a polymer containing phosphorylcholine groups, and has a thickness from 10 to 200 nm,
wherein the substrate and the biocompatible material layer are joined via a binder layer formed from silica covalently bonded with the hydroxyl groups and the biocompatible material, and
wherein the silica comprises a photopolymerization initiator.

16. The sliding member according to claim 15, wherein the biocompatible material layer has a thickness from 100 to 200 nm.

17. A prosthesis comprising the sliding member claimed in claim 16.

18. The sliding member according to claim 15, wherein the biocompatible material layer has wettability defined as a contact angle of 30° or less of the biocompatible material layer to water.

19. The sliding member according to claim 18, wherein the phosphorylcholine groups have a concentration of phosphorus atoms measured by an X-ray photoelectron spectroscopy in a sliding surface of 4.6 atomic % or more.

20. A prosthesis comprising the sliding member claimed in claim 19.

21. A prosthesis comprising the sliding member claimed in claim 18.

22. A prosthesis comprising the sliding member claimed in claim 15.

23. The sliding member according to claim 15, which is a hip joint prostheses, a shoulder joint prostheses, a vertebral prostheses, a knee joint prostheses, an elbow joint prostheses, an ankle joint prostheses, a finger joint prostheses, or an artificial disc, and
wherein the substrate is formed from a ceramic or a cobalt-chromium alloy.

* * * * *